United States Patent [19]
Aikins et al.

[11] Patent Number: 5,453,502
[45] Date of Patent: Sep. 26, 1995

[54] 1,3,4 SUBSTITUTED AND BICYCLIC DERIVATIVES OF 2-AZETIDINONES AND PROCESSES FOR PREPARATION THEREOF

[75] Inventors: James A. Aikins; Larry C. Blaszczak, both of Indianapolis; Kevin P. Lund, Greenwood; John R. Rizzo, Indianapolis, all of Ind.

[73] Assignee: Eli Lilly and Company, Indianapolis, Ind.

[21] Appl. No.: 213,644

[22] Filed: Mar. 16, 1994

[51] Int. Cl.$^6$ .................. C07D 205/095; C07D 205/12; C07D 205/085

[52] U.S. Cl. .................. 540/203; 540/354; 540/358; 540/359; 540/360; 540/364

[58] Field of Search .............................. 540/203

[56] References Cited

U.S. PATENT DOCUMENTS

| | | | |
|---|---|---|---|
| 4,057,540 | 11/1977 | Micetich | 540/203 |
| 4,939,249 | 7/1990 | Blaszczak | 540/205 |
| 5,126,446 | 6/1992 | Brown et al. | 540/230 |

OTHER PUBLICATIONS

Hatanaka, Tet. Letters 24, pp. 4837–4838. (1983).
L. Blaszczak et al., Tetrahedron Letters, 31(40):5693–5696 (1990).
S. Hanessian et al., Tetrahedron Letters 27(40):4857–4860 (1986).
C. Whitesitt et al., Tetrahedron Letters, vol. 20, pp. 1737–1740 (1978).
A. Beckwith et al., J. Chem. Soc., Chem. Commun., pp. 189–190 (1986) "Stereochemistry of Intramolecular Homolytic Substitution at the Sulphur Atom of a Chiral Sulphoxide".
T. Kamestani et al., J. Org. Chem. 53:2683–2687 (1988).
K. P. Lund et al., (Abstract No. 387 Am. Chem. Soc., Div. of Org. Chem., 207th ACS National Meeting, San Diego, Calif., Mar. 13–17, 1994.

*Primary Examiner*—Mark L. Berch
*Attorney, Agent, or Firm*—Thomas G. Plant; Gerald V. Dahling; David E. Boone

[57] ABSTRACT

The invention provides 1,3,4 substituted and bicyclic derivatives of 2-azetidinones and processes therefor. These compounds are valuable intermediates useful in the preparation of 1-carba(dethia)cephalosporin antibiotics.

1 Claim, No Drawings

1,3,4 SUBSTITUTED AND BICYCLIC DERIVATIVES OF 2-AZETIDINONES AND PROCESSES FOR PREPARATION THEREOF

BACKGROUND OF THE INVENTION

This invention relates to β-lactam antibiotics. In particular, it relates to intermediates useful in the preparation of 1-carba(dethia)carbacephalosporin antibiotics.

In contrast to the cephalosporin antibiotics, which are prepared semisynthetically, 1-carba(dethia)carbacephalosporins have thus far been obtained, for the most part, by totally synthetic methods. For example, Christensen et al., U.S. Pat. No. 4,226,866, describe a method for the preparation of 1-carba(dethia)carbacephalosporin antibiotics. Also, Evans et al., U.S. Pat. No 4,665,171, describe an asymmetric total synthesis of the amino-protected 3-hydroxy-1-carba(dethia)carbacephalosporin nucleus ester. Morin et al., U.S. Pat. No. 4,885,362, describe a semisynthetic method wherein utilizing azetidinone-2 intermediates in the preparation of 1-carba(dethia)carbacephalosporins. Because of the growing importance of 1-carba(dethia)carbacephalosporins as therapeutic agents for the treatment of infectious diseases, intermediates and methods useful in the preparation thereof are of considerable value.

SUMMARY OF THE INVENTION

The present invention provides compounds of the formula (I):

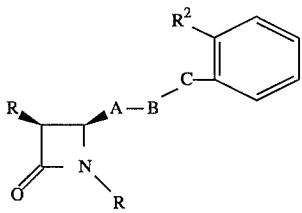

wherein R is an amino group; a protector amino group; or a group of the formula —$NR^aR^b$, wherein $R^a$ is an amino protecting group and $R^b$ is selected from the group consisting of acryloyl and α-substituted acryloyl; $R^1$ is hydrogen or an amide protecting group; $R^2$ is a radical forming group; A is —S— or —$(SO)_n$—, wherein n is 0 or 1; and B and C are independently selected from a group consisting of oxygen, sulfur, methylene, selenium, and nitrogen. Compounds of formula (I) wherein R is an amino group or a protected amino group are designated herein as formula (Ia) compounds. Compounds of formula (I) wherein R is a group of the formula —$NR^aR^b$, as defined above, are designated herein as formula (Ib) compounds.

In another embodiment, the invention provides compounds of the formula (II):

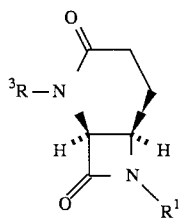

wherein $R^1$ is a hydrogen or an amide protecting group; and $R^3$ is hydrogen or an amino protecting group. Compounds of formula (II) wherein $R^3$ is hydrogen are designated herein as formula (IIa) compounds. Compounds of formula (II) wherein $R^3$ is an amino protecting group, are designated herein as formula (IIb) compounds.

The invention also provides a process for preparing a compound of the formula (Ia) which comprises reacting a compound of the formula (III):

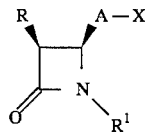

wherein X is halogen, R is a protected amino group, and $R^1$ and A are as defined for the formula (I) compounds; with a substituted benzyl of the formula:

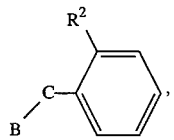

wherein B, C, and $R^2$ are as defined for the formula (I) compounds, said reaction conducted under substantially anhydrous conditions for a time and at a temperature sufficient to result in a compound of formula (Ia).

In another embodiment, the invention provides a process for preparing a compound of the formula (Ib) which comprises reacting a compound of the formula (Ia) with a tertiary alkoxide and an acyl chloride under substantially anhydrous conditions for a time and at a temperature sufficient to result in a compound of formula (Ib).

The invention also provides a process for preparing a compound of the formula (IIa) which comprises reacting a radical producing agent with a compound of the formula (Ib) under substantially anhydrous conditions for a time and at a temperature sufficient to result in a compound of formula (IIa).

DETAILED DESCRIPTION OF THE INVENTION

This invention provides compounds and processes that allow for an efficient means of producing known intermediates useful in the production of 1-carba(dethia)carbacephalosporins. These intermediates can be produced from penicillin V or similar economically advantageous starting compounds. These known 1-carba(dethia)carbacephalosporin intermediates are described in U.S. Pat. No. 4,885,362, which is incorporated herein by reference.

The term "protected amino" as employed herein, are those conventional protecting or blocking groups commonly employed for the temporary protection of an amino group, covalently bonded to the amino group being protected. The term "amino protecting group" are such conventional protecting or blocking groups not in combination with the amino group being protected. Such groups are frequently used during preparation of a compound to prevent unwanted side reactions involving an unprotected amino group. For example, an amino group is protected or blocked when it might compete with an acylation reaction or esterification reagent directed at another site in the same molecule.

Examples of such conventional protecting groups include the aryl, alkyl, cycloalkyl or bicyclo-oxycarbonyl groups. The term "amino protecting group" also includes groups of the formula:

wherein $R^{11}$ is a residue of a carboxylic acid.

The term "residue of a carboxylic acid" includes those 7-position side chains known in the cephalosporin and carbacephalosporin arts, and those 6-position side chains known in the penicillin art, wherein $R^{11}$ of the formula:

may be a $C_1$–$C_{20}$ residue of a carboxylic acid. The term "$C_1$–$C_{20}$ residue of a carboxylic acid" includes such groups wherein $R^{11}$ is hydrogen, $C_1$–$C_6$ alkyl, $C_1$–$C_6$ alkyl substituted by cyano, carboxy, halogen, amino, $C_1$–$C_4$ alkoxy, $C_1$–$C_4$ alkylthio, trifluoromethyl, trifluoromethylthio, naphthyl, phenyl or a substituted phenyl group represented by the formula:

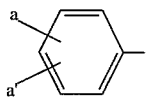

wherein a and a' independently are hydrogen, hydroxy, cyano, $C_1$–$C_4$ alkoxy, $C_1$–$C_4$ alkanoyloxy, $C_1$–$C_4$ alkyl, $C_1$–$C_4$ alkylthio, amino, $C_1$–$C_4$ alkanoylamino, $C_1$–$C_4$ alkylsulfonylamino, carboxy, carbamoyl, hydroxymethyl, aminomethyl, carboxymethyl; or $R^{11}$ is a group represented by the formula:

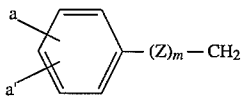

wherein a and a' are defined as above, Z is O or S, and m is 0 or 1; or $R_{11}$ is an arylmethyl group represented by the formula:

wherein $R^5$ is naphthyl, thienyl, furyl, benzothienyl, benzofuryl, benzoaminothiazolyl, pyridyl, 4-pyridylthio, pyrimidyl, pyridazinyl, pyrazolyl, imidazolyl, indolyl, triazolyl, tetrazolyl, oxazolyl, thiazolyl, oxadiazolyl, thiadiazolyl, and such aryl groups substituted by amino, hydroxy, cyano, $C_1$–$C_4$ alkyl, $C_1$–$C_4$ alkoxy, phenyl, substituted phenyl or $C_1$–$C_4$ alkylsulfonylamino; or $R^{11}$ is a substituted methyl group represented by the formula:

wherein $R^6$ is cyclohex-1,4-dienyl, or an optionally substituted phenyl group respresented by the formula:

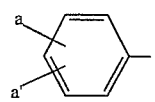

wherein a and a' have the above defined meanings, or $R^6$ is $R^5$ as defined above, and Q is amino, protected amino, sulfo, hydroxy, $C_1$–$C_4$ alkanoyloxy, carboxy, sulfoamino, or Q is a substituted amino group of the formula:

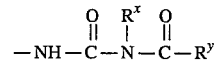

Wherein $R^x$ is hydrogen or $C_1$–$C_3$ alkyl, $R^y$ is $C_1$–$C_4$ alkyl, furyl, thienyl, phenyl, styryl, or a group of the formula:

wherein $R^x$ has the same meanings as defined above and $R^z$ is hydrogen, $C_1$–$C_3$ alkylsulfonyl, $C_1$–$C_3$ alkyl, or $C_1$–$C_4$ alkanoyl; or Q is a substituted amino group of the formula:

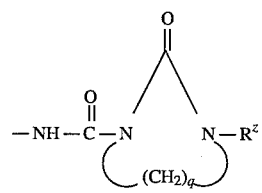

wherein $R^z$ has the same meanings as defined above, and q is 2 or 3; or Q is a substituted amino group of the formula:

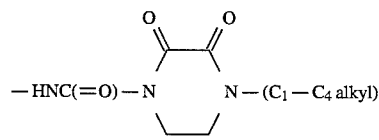

or Q is a benzamido group of the formula:

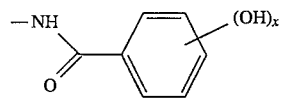

wherein X is 1 to 3; or Q is a pyridone or pyridonylcarbonylamino group of the formula:

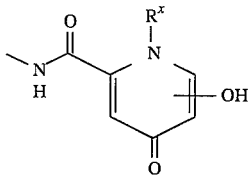

wherein $R^x$ is as defined above; or Q is a pyridylcarbonylamino group of the formula:

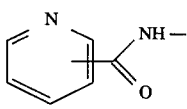

said group optionally substituted by $C_1$-$C_4$ alkyl, amino, carboxy, hydroxy or halogen; or Q is an imidazolyl or pyrazolyl group of the formula:

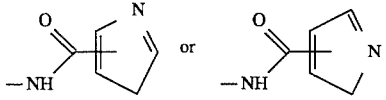

and such imidazolyl or pyrazolyl optionally substituted by $C_1$-$C_4$ alkyl, carboxy, amino; or Q is a benzpyridazin-4-one group or tautomer thereof represented by the formula:

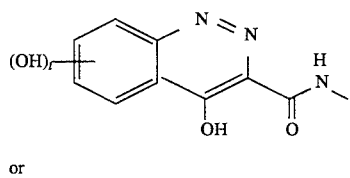

or

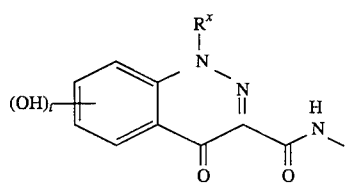

wherein $R^x$ is as defined above and t is 1 to 3; or Q is a benzpyranone group of the formula:

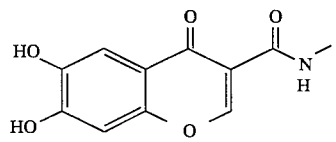

or R is a group represented by the formula:

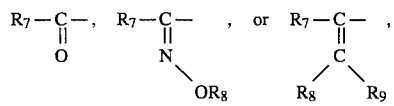

wherein $R_7$ is $R_5$ or $R_6$ as defined above, $R_9$ is hydrogen, and $R_8$ is hydrogen, $C_1$-$C_4$ alkyl, or a carboxy-substituted alkyl or cycloalkyl group represented by the formula:

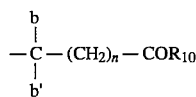

wherein b and b' independently are hydrogen or $C_1$-$C_3$ alkyl, or b and b', when taken together with the carbon to which they are bonded, form a 3- to 6-membered carbocyclic ring, n is 0–3, and $R_{10}$ is hydroxy, $C_1$-$C_4$ alkoxy, amino, $C_1$-$C_4$ alkylamino, or di($C_1$-$C_4$ alkyl) amino; or $R_8$ is $C_1$-$C_4$ substituted by phenyl or phenyl substituted by one or two of the same or different groups selected from among $C_1$-$C_4$ alkyl, hydroxy, carboxy or protected carboxy; or $R_8$ is $C_1$-$C_4$ alkyl substituted by amino or protected amino; or $R_8$ is $C_2$-$C_4$ alkenyl; or $R_8$ is a cyclic lactam group of the formula:

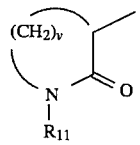

wherein v is 2–4 and $R_{11}$ is hydrogen or $C_1$-$C_3$ alkyl; or $R_8$ is an arylmethyl group of the formula:

$R^5$—$CH_2$— wherein $R^5$ has the same meanings as defined hereinabove.

The amino protecting group can also be an enamine such as is formed with a free amino group and a β-keto ester or β-diketone such as for example, ethyl acetoacetate, methyl acetoacetate, acetylacetone or benzoylacetone and the like. Other conventional protecting groups include triphenylmethylamino, diphenylmethylamino, 4,5-diphenyl-4-oxazolin-2-one-1-yl. Protecting groups commonly employed for amino groups are described in more detail in E. Haslam, "Protective Groups in Organic Chemistry", J. G. W. McComie, ed., Plenum Press, New York, N.Y. 1973, and by Greene, "Protective Groups in Organic Synthesis", John Wiley & Sons, New York, N.Y. 1981.

As used herein the term "amide protecting group" refers to any group typically used in the β-lactam art for protecting the β-lactam ring nitrogen from undesirable side reactions. Such groups include esters and amides of 2-(3-methyl)-3-butenoic acid and 2-(3-methyl)- 2-butenoic acid [i.e., the 1,2-seco-penicillin residue] p-methoxyphenyl, 3,4-dimethoxybenzyl, benzyl, O-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, tri($C_1$-$C_4$ alkyl)silyl, triphenylmethylsilyl, diphenylmethylsilyl, benzylsilyl, and the like. Protecting groups commonly employed for amide groups are described in more detail by E. Haslan in "Protective Groups in Organic Chemistry", J. G. W. McComie, Ed., Plenum Press, New York, N.Y. 1973, and by T. Greene in "Protective Groups in Organic Synthesis", John Wiley & Sons, New York, N.Y. 1981, both of which are incorporated by reference.

In the above definitions, amino, and amide protecting groups are not exhaustively defined. Many protecting groups groups are known in the art, and the use of other protecting groups not specifically referred to hereinabove are equally applicable to the present invention.

With reference to the terms used above, "$C_1$-$C_6$ alkyl" refers to the straight and branched chain alkyl groups such as methyl, ethyl, n-propyl, iso-propyl, n-butyl, iso-butyl, t-butyl, n-pentyl, neopentyl, n-hexyl, and the like; "$C_2$-$C_6$ alkenyl" refers to 3-pentenyl, and the like; "$C_1$-$C_4$ alkoxy" refers to methoxy, ethoxy, propoxy, t-butoxy, n-butoxy and the like; "$C_1$-$C_4$ alkylthio" refers to methylthio, ethylthio, propylthio, n-butylthio and the like; "tri($C_1$-$C_4$ alkyl)silyl" refers to trimethylsilyl, triethylsilyl, tri-(n-butyl)silyl, t-butyldimethylsilyl, and like groups, "$C_2$-$C_6$ alkanoyloxy"

refers to acetoxy, propionoxy, butyyloxy, and the like; "substituted acryloyl" refers to 2-substituted acryloyl or 3-substituted acryloyl groups. The acryloyl group can be substituted by a wide variety of substituents. However, the 2 or 3 position substitutent must not be a radical chain terminating group such as —$NO_2$.

The term "radical forming group" represents those groups recognized in free radical chemistry that readily provide a carbon-centered free radical upon subjection to free radical-generating conditions. In the context of this invention, the $R^2$ group may be any group affording a compound of the general formula:

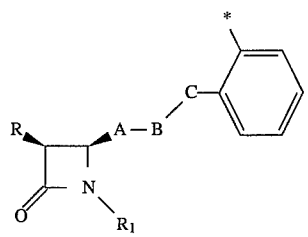

wherein * represents a free radical. While a number of such groups are known, specific examples are described in U.S. Pat. No. 4,939,249, which is herein incorporated by reference. Such described examples include halogen, selenides, $R^{15}Se$— or sulfides, $R^{15}S$—, wherein $R^{15}$ is $C_1$-$C_6$ alkyl, $C_3$-$C_8$ cycloalkyl, $C_2$-$C_6$ alkenyl, $C_2$-$C_6$ alkynyl, phenyl, naphthyl, pyrimidinyl, tetrazolyl, pyridinyl, benzothienyl, or benzofuryl. Other groups include a carboxy group, a thiocarbonate of the formula ArOC(S)O— or ArS.C(S) O—, wherein Ar is phenyl, or naphthyl; or a heterocyclic thione ester, for example, (N-pyridyl-2-thione)oxycarbonyl and (N-pyrimidyl-2-thione)oxycarbonyl.

The term "radical producing agent" as employed in the above processes are free radical initiators, and include organic radical producing agents (discussed below). Examples of such free radical initiators are described in U.S. Pat. No. 4,939,249, and include: UV radiation produced, for example, by a mercury-vapor lamp or the like; a peroxide such as dibenzoyl peroxide; an organo tin hydride such as tri($C_1$-$C_4$ alkyl)tin hydride, substituted trialkyltin such as methallyl tributyltin; a triaryltin hydride, $(R_{18})_3SnH$, wherein $R_{18}$ is phenyl, $C_1$-$C_4$ alkylphenyl, chlorophenyl; a triaryltin hydride such as tribenzyltin hydride and substituted tribenzyltin hydrides, for example, tri-(4-methylbenzyl)tin hydride, and like organotin hydrides; a trialkylgermane, for example, triethylgermane, or a triarylgermane such as triphenylgermane.

The following scheme illustrates processes and intermediates encompassed by the invention and their use in the ultimate preparation of carbacephalosporin precursors.

REACTION SCHEME

STEP ONE

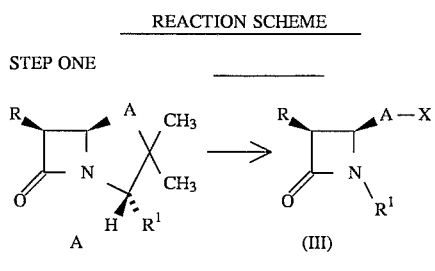

STEP TWO

STEP THREE

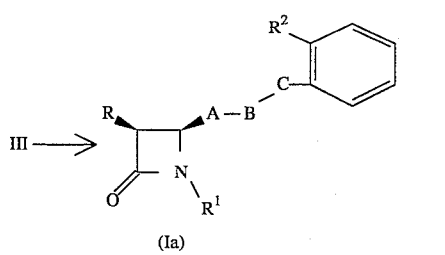

STEP FOUR

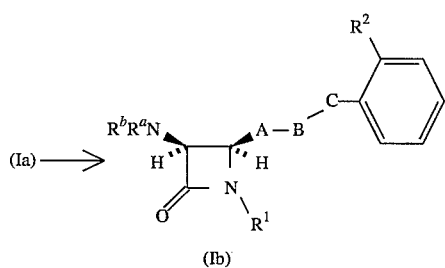

STEP FIVE

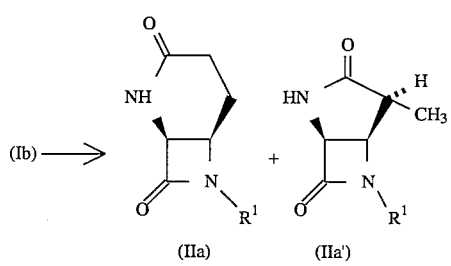

STEP SIX

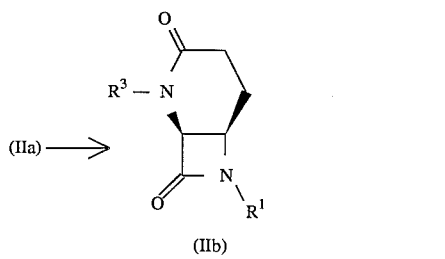

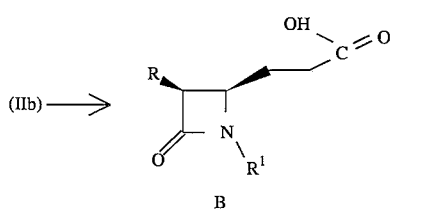

Compounds of Formula (A) and (III) in Step One, above, are described in U.S. Pat. No. 4,081,440, which is incorporated herein by reference. Step One of the above scheme is carried out generally as follows. A formula (A) compound is heated in an inert organic solvent in the presence of an insoluble base and a positive halogen source. The solution is refluxed at a temperature of about 75° C. to about 120° C. then cooled to about −10° C. forming a compound of formula (III). The resulting reaction mixture is filtered and the filtrate is used in Step Two. Substituents A, X, and R¹ of the formula (A) and (III) compounds are as previously defined for the formula (III) compounds.

Preferred solvents for Step One and subsequent reaction steps are aprotic and include aromatic hydrocarbons such as toluene, benzene, xylene, chlorobenzene and the like, and halogenated hydrocarbons such as chloroform, methylene chloride, carbon tetrachloride, and the like. Especially preferred solvents are toluene and benzene. Preferred insoluble bases include polyvinylpyridine, poly-diisopropylvinylamine, copoly-vinylpyridinedivinylbenzene (PVP-DVB), and calcium oxide. Preferred positive halogen sources include N-chlorosuccinimide and N-chlorophthalimide, the latter being more preferred. An illustrative example of Step One of the Reaction Scheme is provided in Example 1.

Step Two of the Reaction Scheme provides a compound of formula (Ia) and is carried out generally as follows. The filtrate containing the formula (III) compound, obtained in Step One, is mixed with a tertiary amine and a radical producing agent of the formula:

(IV)

wherein substituents B, C, and R² are as previously defined for the formula (IV) compounds. Preferred tertiary amine bases include pyridine, triethylamine, and diisopropylamine. Diisopropylamine is the most preferred. Preferred radical producing agents include o-bromobenzyl alcohol, o-diazoniumbenzyl alcohol, and o-iodobenzyl alcohol being most preferred.

The Step Two reaction is conducted at a temperature of about 0° C. to about 25° C. for about 60 minutes. The reaction mixture is then diluted with ethyl acetate, and extracted with N HCl. The resulting product is dried and the solvent is removed. The product is then crystallized using standard procedures. An illustrative example of the Step Two reaction is also provided in Example 1.

Step Three of the Reaction Scheme is generally carried out as follows. A formula (Ia) compound from Step Two of the Reaction Scheme is dissolved in an inert solvent, as describe above, and a tertiary amine such as triethylamine (TEA) is added. After stirring from about 60 minutes to about 180 minutes, the solvent and the TEA are removed by rotary evaporation producing an oil. The oil is dissolved in tetrahydrofuran (THF) and the mixture is cooled to a temperature of about −80° C. to about −65° C. for about 30 minutes. A solution of a tertiary alkoxide in an inert solvent, preferably THF, is slowly added to the mixture. Examples of tertiary alkoxides include sodium t-butoxide, potassium t-butoxide, lithium t-butoxide and lithium t-amyl oxide. Lithium tetriary alkoxides are more preferred. Lithium t-butoxide is most preferred. A THF solution of acryloyl chloride, 2-substituted acryloyl chloride or 3-substituted acryloyl chloride is added slowly and the reaction temperature is maintained between −80° C. and −65° C. for about 30 minutes. 2-bromoacryloyl is most preferred because it provides primarily the compound of formula (IIa) in the next step of the Reaction Scheme. Radical chain terminating groups such as —NO₂ are the only limit to 2- or 3-substitution on the acryloyl group. Substitution at position 2 of the acryloyl group is preferred; 2-bromo is the most preferred. The reaction is quenched at −80° C. to −65° C. with a dilute solution of acetic acid in THF and allowed to warm to room temperature. The solution is diluted with ether and extracted with pH 7 buffer and brine. The resulting mixture is dried and then isolated using standard procedures resulting in a compound of formula (Ib). An illustrative example of the Step Three reaction is also provided in Example 2.

Step Four of the reaction scheme yields a compound of the formula (IIa) and is an intramolecular example of the chemistry described in B. Giese, Radicals in Organic Synthesis: Formation of Carbon-Carbon Bonds, J. E. Baldwin, Ed.; Pergammon Press: New York, 1986; Chapter 2, pp. 4–11]. and is carried out generally as follows. A compound of the formula (Ib) is dissolved in an inert aromatic solvent such and benzene, toluene, or xylene along with trialkyl ($C_1$ to $C_6$ alkyl) or triaryl (phenyl or alkyl substituted phenyl) stannane in euqivalent to three times equivalent amount. The aromatic solvent must not be substitued by —NO2 (radical chain terminator) or halogen (reaction competitive with compounds of the formula Ib). A radical chain reaction (B. Giese, 1986, supra.) is initiated in a manner appropriate to the particular radical forming group. Preferred methods are irradiation of the mixture through quartz at 0° C. to 25° C. with light from 2000 Å to 3000 Å or heating from 70° C. to 120° C. in the presence of an initiator such as 2,2'-azobis [isobutyronitrile] (AIBN) or dibenzoyl peroxide. The most preferred method is heating in the presence of AIBN. After a reaction time of 10 minutes to 60 minutes, the mixture is cooled to 25° C. and the solvent removed by evaporation in vacuo. The residue is partitioned in a two phase mixture of pentane and acetonitrile. The tin containing materials are removed in the pentane phase and the products are contained in the acetonitrile phase. The acetonitrile is removed by evaporation in vacuo. The residue is taken up in THF and treated with an equivalent amount of aqueous N lithium hydroxide at 0° C. to 25° C. When the reaction is judged to be complete by thin-layer chromatographic analysis (tlc), it is quenched by the addition of an equivalent amount of N aqueous HCl and partitioned between ethyl acetate and water. The organic phase is dried and concentrated in vacuo and the residue is chromatographed on silica gel thereby isolating the desired product (compounds of the formula IIa) from the by-product (compounds of the formula IIa'). The product is formed by radical reaction at the terminal vinylic carbon of the acryloyl group; the by-product is formed by radical reaction at the internal vinylic carbon. An illustrative example of Step Four of the reaction scheme is provided in Example 3.

Step Five of the Reaction Scheme yields a compound of the formula IIb and is carried out generally as follows. A compound of the formula IIa is acylated with di(tert-butyl)dicarbonate, 4 -N,N-dimethylaminopyridine, and triethylamine according to the procedure of U.S. Pat. No. 5,239,068 the entire contents of which are incorporated herein. The product of this acylation reaction is dissolved in acetone and cooled from 0° C. to 5° C. A solution of potassium permanganate in 0.25M phosphate buffer at pH 7 is added dropwise during about 10 minutes to about 60 minutes. Stirring is contiunued at 0° C. to 5° C. for approximately 30 minutes and then diluted with water followed by extraction with ethyl acetate. The ethyl acetate solution is extracted with brine, dried, and concentrated to a solid residue, a compound of the formula IIb wherein R¹=H. An illustrative example of Step Five of the reaction scheme is provided in Example 4.

Compound (IIb) is a useful in forming the known azetidione of the formula (B). Formula (B) compounds are described in U.S. Pat. No. 4,885,362, and are useful as intermediates in the production of 1-carba(dethia)cephalosporins such as loracarbef. Step Six of the reaction scheme yields a formula (B) compound by a three step procedure which comprises reacting a compound of the formula (IIb) sequentially with hydroxide ion to open the six-membered ring, with a volatile strong acid to remove the t-butoxycarbonyl group, and with an acyl chloride and base to effect acylation. The procedure is carried out generally as follows. A formula (IIb) compound is dissolved at about 25° C. in an inert, water miscible solvent, such as THF, 1,4-doxane, or acetonitrile. THF is most preferred. An amount of water equal to 10% of the organic solvent volume is added. A two times equivalent amount of aqueous N lithium hydroxide solution is added slowly with stirring followed by stirring an additional 10 to 60 minutes at 25° C. When the reaction is judged complete by tlc analysis, an amount of chloroform/ isopropyl alcohol mixture (3:1=v/v) sufficient to cause phase separation is added and the pH is adjusted to 4 with aqueous HCl. The organic phase is separated, dried, and concentrated. The residue is taken up in an inert halogenated solvent such as methylene chloride, chloroform, or dichloroethane. Methylene chloride is preferred. A carbonium ion quenching agent such as triphenyl methane, thioanisole, or trialkyl silane is added. Triethyl silane is preferred. The solution is cooled to about 5° C. and trifluoroacetic acid is added in large excess. The mixture is stirred at about 5° C. for about 60 minutes to about 180 minutes. The entire reaction mixture is then concentrated in vacuo. The residue is taken up in acetone/water (1:1=v/v) and submitted to standard Schotten-Baumann acylation conditions at pH 8.0–9.0. When the acylation is complete as judged by tlc analysis, the reaction mixture is extracted with ether to remove neutral materials, acidified to pH 2, and extracted with chloroform. The organic phase is dried and concetrated to afford product B. Substituents R and $R^1$ are as previously defined for the formula (I) compounds. An illustrative example of Step Six of the Reaction Scheme is provided in Examples 6 and 7.

In order to illustrate more fully the operation of this invention, the following examples are provided, but are not to be construed as a limitation on the scope of the invention.

EXAMPLE 1

Synthesis of methyl-2{4β-(2-iodobenzenyloxsulfinyl)-3β-phenoxyacetamido-2-oxo-1-azetidine}-2-(2-propenyl) acetate

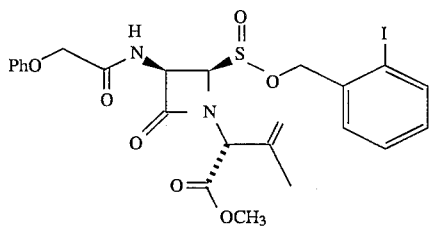

PVP-DVB (7.50 g) was suspended in 450 mL of toluene. Using a Dean-Stark trap, 150 mL of toluene was azeotropically distilled from the solution. The solution was cooled slightly and penicillin sulfoxide methyl ester (16.74 g, 44.00 mmol), N-chlorothalemide (NCP, 9.99 g, 55.0 mmol), and 1-dodecene (19.0 mL, 88.3 mmol) were added. The solution was refluxed for 1.5 hours and then cooled to −5° C. and allowed to sit for 2 hours. The solids were filtered off and the filtrate was allowed to warm to room temperature. o-Iodobenzyl alcohol (12.87 g, 54.99 mmol) was added to the solution followed by diisopropylethyl amine (7.70 mL, 44.2 mmol), and the solution was stirred for 30 minutes at room temperature. The reaction mixture was diluted with ethyl acetate. The mixture was then extracted with 1N HCl $H_2O$, and satuated NaCl. The product was dried over $MgSO_4$ and the solvent was removed in vacuo. Crystallization from $CH_2Cl_2$ and isopropyl ether produced 19.57 g (73%) of methyl-2{4β-(2-iodobenzyloxysulfinyl)- 3β-phenoxyacetamido-2-oxo-1-azetidine)-2-(2-propenyl) acetate.

$^1$H NMR (300 MHz, $CDCl_3$) d 1.78 (s, 3H) 3.78 (s, 3H), 3.78 (s, 3H), 4.47 (s, 2H), 4.86 (s, 1H), 4.89 (s, 1H), 4.98–5.09 (m, 4H), 5.81 (dd, J=9.6, 5.1 Hz, 1H), 6.86 (d, J=8.6 Hz, 2H), 6.99–7.06 (m, 2H), 7.29–7.34 (m, 4H), 7.50 (d, J=9.6 Hz, 1H), 7.82 (d, J=7.9 Hz, 1H).

$^{13}$C NMR (75 MHz, $CDCl_3$) d 20.8, 52.8, 56.8, 61.5, 67.0, 75.5, 75.8, 98.5, 114.9, 118.0, 122.3, 128.7, 129.8, 130.0, 130.7, 137.4, 137.8, 139.7, 156.9, 165.8, 168.4, 168.6.

IR ($CHCl_3$) 3405, 3028, 3013, 1787, 1746, 1696, 1600, 1519, 1496, 1440 $cm^{-1}$. MS (FD+) m/e 613($M^+$+1, 4), 333(58), 331(100), 330(12), 218(12), 217(78), 166(21) 154(20)

Elemental Analysis: $C_{24}H_{25}N_2IO_7S$: Theory: C, 47.07; H, 4.12; N, 4.57; Found: C, 46.97; H, 3.96; N, 4.72. $[a]_D$=−0.5980° (C=0.01 in MeOH).

EXAMPLE 2

Synthesis of Synthesis of methyl-2{4β-(2-iodobenzyloxysulfinyl)-3β-phenoxyacetacrylimido-2-oxo-1-azetidine}-2-isopropylidine acetate

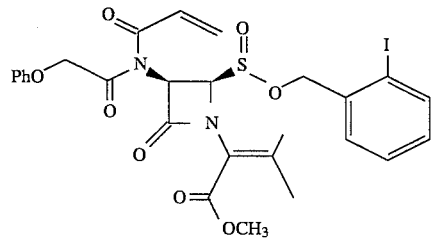

Methyl-2{4β-(2-iodobenzyloxysulfinyl)-3β-phenoxyacetamido-2-oxo-1-azetidine} -2-(2-propenyl) (9.31 g, 15.2 mmol) was dissolved in 200 mL of $CH_2Cl_2$. Triethylamine (10.6 mL, 76.1 mmol), was added and stirred for 1 hour at room temperature. The triethylamine and $CH_2Cl_2$ were removed in vacuo, and the resulting oil was dissolved in 200 mL of tetrahydrofuran (THF), and cooled to −78° C. A 0.64M solution of lithium t-butoxide in THF (47.5 mL, 30.4 mmol) was slowly added over 25 minutes, and after stirring for an additional 15 minutes, acryloyl chloride (6.15 mL, 76.0 mmol) was added dropwise. After stirring for 15 minutes the solution was quenched with saturated $NaHCO_3$ and allowed to warm to room temperature. The solution was diluted with ethanoic acid (EtOAc), extracted with $H_2O$ and brine, and dried over $MgSO_4$. Crystallization from $CH_2Cl_2$ and diisopropyl ether provided 8.93 g (88%) of methyl-2{4β-(2-iodobenzyloxysulfinyl)-3β-phenoxyacetacrylamindo-2-oxo-1-azetidine} -2-isopropylidine acetate.

$^1$H NMR (300 MHz, $CDCl_3$) d 2.24 (s, 3H), 2.27 (s, 3H), 3.78 (s, 3H), 4.78 (d, J=16.7 Hz, 1H), 4.92–5.08 (m, 4H), 5.36 (bs, 1H), 5.86 (d, J=9.1 Hz, 1H), 6.33–6.49 (m, 2H), 6.88 (d, J=8.1 Hz, 2H), 6.96–7.03 (m, 2H), 7.26–7.32 (m, 4H), 7.78 (d, J=7.9 Hz, 1H ).

$^{13}$C NMR (75 MHz, CDCl$_3$) d 22.1, 24.1, 52.1, 61.7, 69.3, 74.2, 80.7, 99.0, 115.0, 119.1, 122.1, 128.6, 128.8, 129.5, 130.2, 130.7, 132.8, 137.5, 139.7, 157.3, 163.5, 167.8, 171.5.

IR (CHCl$_3$) 3028, 3019, 3013, 1788, 1723, 1600, 1496 cm$^{-1}$. MS (FD+) m/e 421(5), 385(M$^+$-C$_7$H$_6$IO$_2$S, 100), 331(11), 217(10).

Elemental Analysis: C$_{27}$H$_{27}$N$_2$IO$_8$S: Theory: C, 48.67; H, 4.08; N, 4.20; Found: C, 48.96; H, 4.31; N, 4.40. [a]$_D$= 38.7483° (C=0.01 in MeOH).

EXAMPLE 3

Synthesis of Methyl-2-{6-(3,5-dioxo-4,6-diazabicyclo[4.2.0.]octyl}-2-isopropylidine acetate and Isomeric By-Products

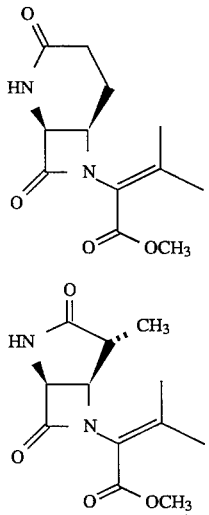

Methyl-2{2β-(2-iodobenzyloxysulfinyl)-3β-phenoxyacetacrylimido-4oxo-1 -azetidine}-2-isopropylidine acetate (5.95 g, 8.93 mmol) was added to 500 mL of toluene and heated at 90° C. until completely dissolved. Tributyltin hydride (2.65 mL, 9.58 mmol) followed by 2,2'-azo bis [isobutyrylnitryl] (AIBN; 366 mg, 2.23 mmol) were added and the solution was heated at 90° C. for 1 hour. Toluene was removed in vacuo and the resulting oil was dissolved in acetonitrile. The mixture was then extracted with pentane to remove the tin impurities. The acetonitrile was removed in vacuo and the resulting oil was dissolved in 100 mL of THF. A 1M solution of LiOH (10 mL, 10 mmol) was added over 50 minutes and stirring was continued for 5 hours. The reaction was quenched with 0.1N acetic acid in THF, warmed to room temperature, diluted with water, and extracted with ethyl acetate. The product was dried over MgSO$_4$, the soluent was removed and chromatographed on silica gel to give methyl-2-{6-(3,5-dioxo-4,6-diazabicyclo [4.2.0.]octyl}-2-isopropylidine acetate (315 mg, 14%) and the isomeric by-products (321 mg, 15%).

methyl-2-{6-(3,5-dioxo-4,6-diazabicyclo[4.2.0.]octyl}-2-isopropylidine acetate:

$^1$H NMR (300 MHz, CDCl$_3$) d 1.73–1.85 (m, 1H), 1.91 (s, 3H), 2.05–2.13 (m, 1H), 2.15 (s, 3H), 2.33–2.39 (m, 1H), 2.47–2.59 (m, 1H), 3.72 (s, 3H), 4.34–4.35 (m, 1H), 4.62 (t, J=5.7 Hz, 1H), 7.27 (s, 1H).

$^{13}$C NMR (75 MHz, CDCl$_3$) d 21.8, 22.4, 23.4, 27.5, 51.8, 53.3, 59.1, 119.6, 151.8, 163.8, 165.6, 172.6.

IR (CHCl$_3$) 3414, 3021, 3011, 2955, 1762, 1723, 1683 cm$^{-1}$.

MS (FD+) m/e 252 (M$^+$, 100), 236(8), 115(8).

isomeric by-products:

$^1$H NMR (300 MHz, CDCl$_3$) d 1.24 (d, J=7.8 Hz, 3H), 1.92 (s, 3H), 2.26 (s, 3H), 2.50 (q, J=7.8 Hz, 1H), 3.78 (s, 3H), 4.28 (d, J=4.7 Hz, 1H), 4.69 (d, J=4.7 Hz, 1H), 6.58 (s, 1H).

$^{13}$C NMR (75 MHz, CDCl$_3$) d 15.4, 21.6, 23.2, 38.3, 51.8, 60.3, 62.6, 118.8, 154.0, 163.7, 165.8, 179.6.

IR (CHCl$_3$) 3431, 3019, 2955, 1762, 1711, 1630 cm$^{-1}$.

MS (FD+) m/e 252(M$^+$, 100), 212(11), 127(10).

EXAMPLE 4

Synthesis of methyl-2-{6-(3,5-dioxo-4-tert-butoxycarbonyl-4,6-diazabicyclo[4.2.0]octyl}-2-isopropylidine acetate

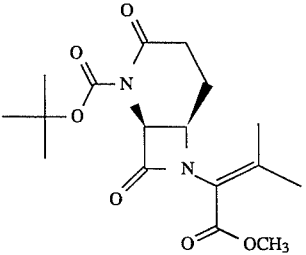

Methyl-2-{6-(3,5-dioxo-4,6-diazabicyclo[4.2.0.]octyl}-2-isopropylidine acetate (226 mg, 0.896 mmol) was (226 mg, 0.896 mmol) was dissolved in 25 mL of CH$_2$Cl$_2$ and 4-[N,N-dimethylaminopyridine] (DMAP; 11 mg, 0.09 mmol) followed by triethylamine (190 μL, 1.36 mmol). Di-t-butyl dicarbonate (320 μL, 1.39 mmol) was dissolved in 10 mL of CH$_2$Cl$_2$ and this solution was slowly added to the reaction mixture over 25 minutes. The resulting reaction mixture was stirred for 8 hours, diluted with EtOAc, and extracted with 1N HCl and brine. The product was dried over MgSO$_4$ and was chromatographed on silica gel to give methyl-2-{6-(3,5-dioxo-4-tert-butoxycarbonyl-4,6-diazabicyclo[4.2.0.]octyl}-2-isopropylidine acetate (281 mg, 89%).

$^1$H NMR (300 MHz, CDCl$_3$) d 155 (s, 9H), 1.81–1.95 (m, 1H), 1.96 (s, 3H), 2.08–2.19 (m, 1H), 2.20 (s, 3H), 2.50–2.59 (m, 1H), 2.74–2.87 (m, 1H), 3.76 (s, 3H), 4.37–4.42 (m, 1H), 5.26 (d, J=6.1 Hz, 1H).

$^{13}$C NMR (75 MHz, CDCl$_3$) d 22.0, 22.6, 23.4, 23.4, 27.9, 30.2, 52.0, 54.3, 60.4, 84.4, 119.8, 151.3, 152.6, 164.0, 164.7, 169.5. IR (CHCl$_3$) 3023, 2986, 2955, 1771, 1729, 1631 cm$^{-1}$.

MS (FD+) m/e 352(M$^+$, 18), 252(12), 197(36), 155(100), 131(9), 114(8), 97(26).

Elemental Analysis: C$_{17}$H$_{24}$N$_2$O$_6$: Theory: C, 57.94; H, 6.86; N, 7.95; Found: C, 57.74; H, 6.68; N, 7.94.

[a]$_D$=–22.6667° (C=0.0015 in MeOH).

EXAMPLE 5

Synthesis of 3,5-dioxo-4-tert-butoxycarbonyl-4,6-diazabicyclo[4.2.0.]octane

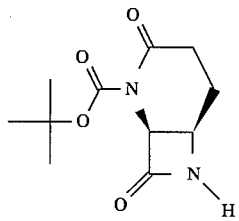

KMnO$_4$ (111 mg, 0.702 mmol) was dissolved in 15 mL of H$_2$O and 10 mL of pH 7 buffer. This solution was added dropwise over 25 minutes to a solution of methyl-2-{6-(3,5-dioxo-4-tert-butoxycarbonyl-4,6 -diazabicyclo[4.2.0.]-octyl}-2-isopropylidine acetate (248 mg, 0.704 mmol) in 50 mL of acetone at 0° C. The mixture was stirred an additional 25 minutes, diluted with H$_2$O, and extracted with EtOAc. The resulting mixture was diluted with ethyl acetate, extracted with brine, and dried over MgSO$_4$. The ethyl acetate solution was concentrated in vacuo and the residue chromatographed on silica gel to give 3,5-dioxo-4-tert-butoxycarbonyl-4,6 -diazabicyclo[4.2.0.]octane (281 mg, 89%).

$^1$H NMR (300 MHz, CD$_3$CN) d 1.50 (s, 9H), 1.78–1.95 (m, 1H), 2.02–2.14 (m, 1H), 2.33–2.57 (m, 2H), 4.09–4.17 (m, 1H), 5.46 (d, J=5.6 Hz, 1H), 6.46 (bs, 1H).

$^{13}$C NMR (75 MHz, CD$_3$OD) d 25.2, 28.4, 30.6, 63.1, 85.6, 152.8, 169.5, 172.9. IR (CHCl$_3$) 3416, 3020, 2985, 1779, 1732 cm$^{-1}$.

MS (FD+) m/e 241 (M$^+$+H, 71), 231(24), 198(100).

EXAMPLE 6

Synthesis of 2-oxo-3β-(tert-butoxycarbamoyl)-4β-(3-propanoic acid)-1-azetidine

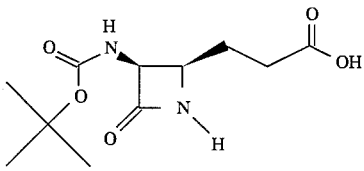

The starting material, 3,5-dioxo-4-tert-butoxycarbonyl-4,6-diazabicyclo[4.2.0.]octane 38.0 mg, 0.158 mmol) was dissolved in 10 mL of THF and 1 mL of H$_2$O. 1N LiOH (320 µL, 320 mmol) was added to the reaction mixture very slowly over 15 minutes. The reaction mixture was stirred an additional 30 minutes and quenched with N aqueous HCl (1 mL). Ten mL of a CHCl$_3$/isopropyl alcohol (3:1) solution was added and stirred rapidly while the solution was acidified to pH 4 with 1N HCl. The organic layer was collected and dried over MgSO$_4$. The solvent was removed and 36.6 mg (89%) of 2-oxo-3β-(tert-butoxycarbamoyl)-4β-(3-propanoic acid)-1 -azetidine was collected.

$^1$H NMR (300 MHz, DMSO-d$_6$) d 1.37 (s, 9H), 1.48–1.68 (m, 2H), 2.11–2.28 (m, 2H), 3.47–3.59 (m, 1H), 4.75 (dd, J=9.2, 4.8 Hz, 1H), 7.68 (d, J=9.6 Hz, 1H), 8.20 (s, 1H), 12.1 (bs, 1H).

$^{13}$C NMR (75 MHz, CDCl$_3$) d 25.8, 28.1, 30.0, 52.7, 59.6, 78.5, 155.3, 167.5, 174.1.

IR (CH$_2$Cl$_2$) 3356, 3009, 2981, 2934, 1746, 1714, 1508 cm$^{-1}$.

MS (FD+) m/e 259 (M$^+$+H,99), 216(12), 215(100).

EXAMPLE 7

Synthesis of 2-oxo-3β-phenoxyacetamido-4β-(3-propanoic acid)-1-azetidine

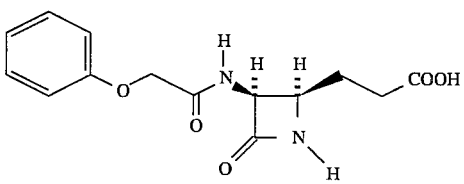

The starting material, 2-oxo-3β-(tert-butoxycarbamoyl)-4β-(3-propanoic acid)-1-azetidine (63 mg, 0.24 mmol) and triethyl silane (0.16 mL, 7 mmol) are dissolved dissolved in dichloromethane (2 mL) and the solution is cooled to 0° C. Trifluoroacetic acid (1 mL) is added and the mixture is stirred at 0° C. for 3 hours. Concentration of the reaction mixture in vacuo affords the trifluoroacetate salt as a waxy solid which is used without further purification.

The crude salt is taken up in acetone (2 mL) and diluted with water (2 mL). The pH is adjusted to 8.5 with 0.1N NaOH. A solution of phenoxyacetyl chloride in acetone (0.1M) is added by microsyringe with stirring and concomitant addition of aqueous NaOH in order to maintain the pH near 8.5. Addition of the acid chloride is discontinued when the pH stabilized at 8.0–8.5; stirring is maintained for 15 minutes. The reaction mixture is partitioned between diethyl ether and water; the ether layer is drawn off and discarded. The aqueous solution is layered with chloroform and the pH is adjusted to 2 with vigorous stirring. The organic phase is separated, dried over MgSO$_4$, and concentrated in vacuo to a solid. The solid is triturated with ethyl acetate and dried to yield 2-oxo-3β-phenoxyacetamido-4β-(3-propanoic acid)-1-azetidine (58 mg, 83%).

$^1$H NMR (300 MHz, DMSO-d$_6$) d 1.65 (m, 2H), 2.20 (m, 2H), 3.64 (m, 1H), 4.57 (ABq, 2H), 5.08 (dd, J=8.0, 4.0 Hz, 1H), 7.30 (m, 2H), 8.38 (s, 1H), 8.92 (d, J=8.0 Hz, 1H), 12.1 (br s, 1H);

IR (KBr) 3321, 1744, 1715, 1665, 1533, 1489, 1235, 1193, and 1181 cm$^{-1}$;

MS (FD+) m/e 293 (M$^+$+H).

We claim:

1. A compound of the formula (II):

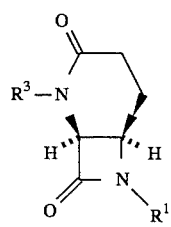
wherein $R^1$ is a hydrogen or an amide protecting group; and $R^3$ is hydrogen.
* * * * *